US009186266B2

(12) United States Patent
Orion et al.

(10) Patent No.: US 9,186,266 B2
(45) Date of Patent: Nov. 17, 2015

(54) EXTERNAL SUPPORT FOR ELONGATED BODILY VESSELS

(75) Inventors: Eyal Orion, Ramat-Efal (IL); Liad Yosef, Holon (IL); Ronny Winshtein, Ramat-HaSharon (IL)

(73) Assignee: VASCULAR GRAFT SOLUTIONS LTD., Tel-Aviv (IL)

( * ) Notice: Subject to any disclaimer, the term of this patent is extended or adjusted under 35 U.S.C. 154(b) by 111 days.

(21) Appl. No.: 14/112,278

(22) PCT Filed: Apr. 3, 2012

(86) PCT No.: PCT/IL2012/050121
§ 371 (c)(1),
(2), (4) Date: Oct. 17, 2013

(87) PCT Pub. No.: WO2012/143922
PCT Pub. Date: Oct. 26, 2012

(65) Prior Publication Data
US 2014/0046432 A1 Feb. 13, 2014

Related U.S. Application Data

(60) Provisional application No. 61/476,347, filed on Apr. 18, 2011.

(51) Int. Cl.
*A61F 2/06* (2013.01)
*A61F 2/95* (2013.01)
(Continued)

(52) U.S. Cl.
CPC ...... *A61F 2/95* (2013.01); *A61F 2/06* (2013.01); *A61B 17/11* (2013.01); *A61B 2017/1107* (2013.01); *A61B 2017/1139* (2013.01); *A61F 2/064* (2013.01); *A61F 2/90* (2013.01)

(58) Field of Classification Search
CPC ........................................................ A61B 17/11
USPC ........................................................ 623/1.11
See application file for complete search history.

(56) References Cited

U.S. PATENT DOCUMENTS 4,743,251 A 5/1988 Barra
2003/0125789 A1* 7/2003 Ross et al. .................... 623/1.11
(Continued)

FOREIGN PATENT DOCUMENTS

WO WO 95/15130 6/1995
WO WO 2004/096095 11/2004
(Continued)

OTHER PUBLICATIONS

International Search Report and the Written Opinion Dated Oct. 1, 2012 From the International Searching Authority Re. Application No. PCT/IL2012/050139.
(Continued)

*Primary Examiner* — Kathleen Holwerda
*Assistant Examiner* — Socrates L Boutsikaris
(74) *Attorney, Agent, or Firm* — Clements Bernard PLLC; Christopher L. Bernard; Lawrence A. Baratta, Jr.

(57) ABSTRACT

An external bodily vessel support comprising an elongate body with a longitudinal axis and an interior to be brought into apposition with an exterior of the bodily vessel. The elongate body including a tubular fabric of a plurality of threads, the body when in a relaxed configuration having a relaxed length and being sized and shaped to fit over of the exterior of the bodily vessel, the tubular fabric being longitudinally elastic to maintain the length with an axial stiffness of at least 0.1 N/m.

17 Claims, 8 Drawing Sheets

(51) Int. Cl.
 *A61B 17/11* (2006.01)
 *A61F 2/90* (2013.01)

(56) References Cited

U.S. PATENT DOCUMENTS

| | | | |
|---|---|---|---|
| 2003/0135265 A1* | 7/2003 | Stinson | 623/1.16 |
| 2004/0215309 A1* | 10/2004 | Moritz et al. | 623/1.5 |
| 2005/0131520 A1* | 6/2005 | Zilla et al. | 623/1.13 |
| 2007/0293932 A1 | 12/2007 | Zilla et al. | |
| 2014/0052234 A1 | 2/2014 | Winshtcin et al. | |

FOREIGN PATENT DOCUMENTS

| | | |
|---|---|---|
| WO | WO 2010/058406 | 5/2010 |
| WO | WO 2012/143922 | 10/2012 |
| WO | WO 2012/143925 | 10/2012 |

OTHER PUBLICATIONS

International Search Report and the Written Opinion Dated Aug. 3, 2012 From the International Searching Authority Re. Application No. PCT/IL2012/050121.

* cited by examiner

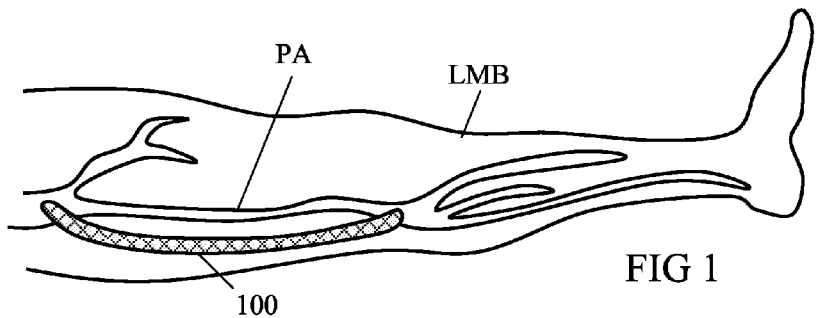
FIG 1
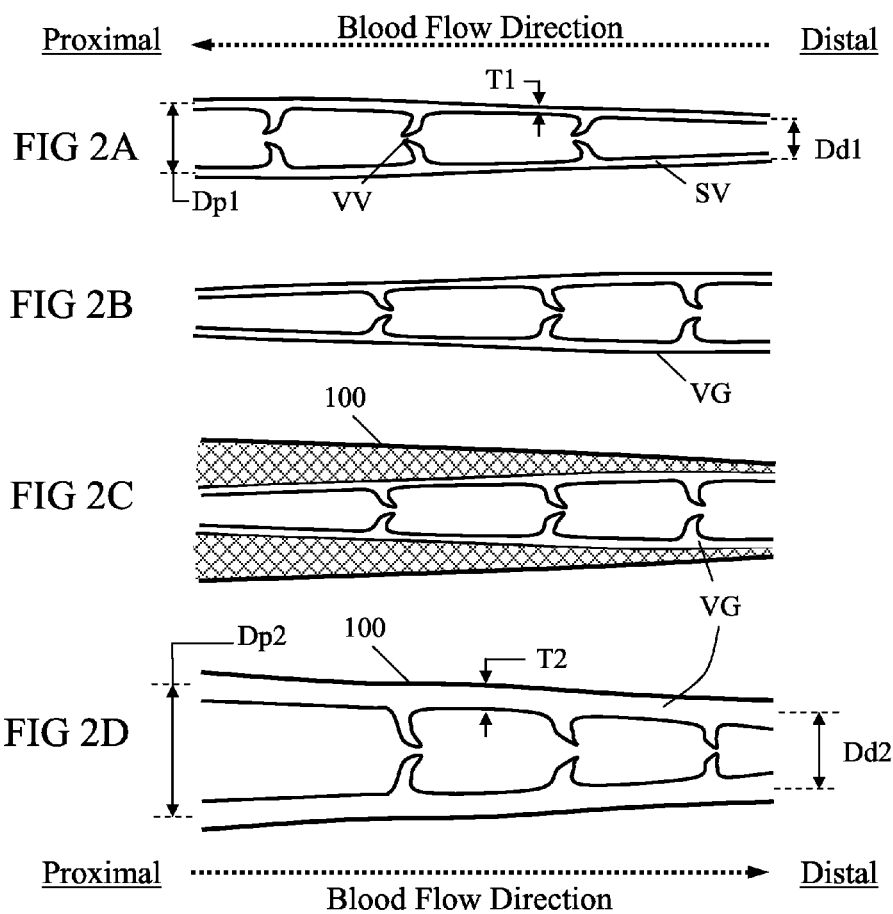

FIG 9D
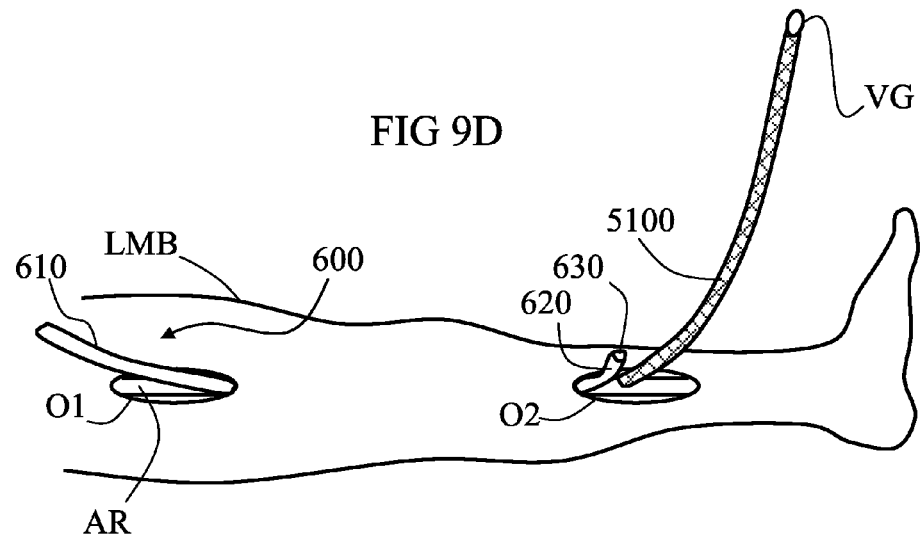
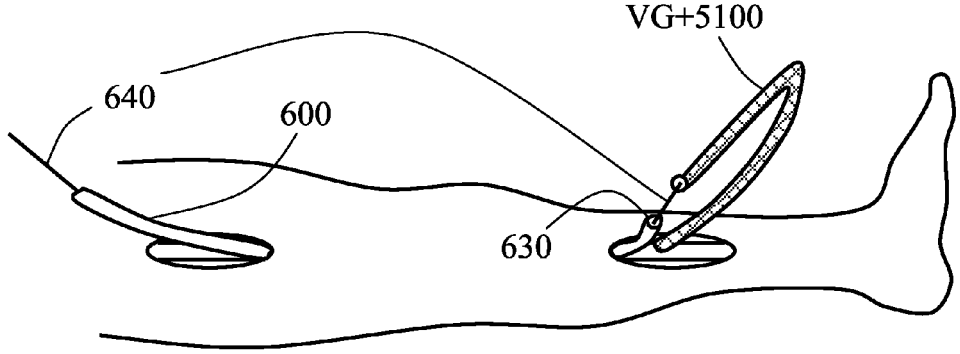
FIG 9E
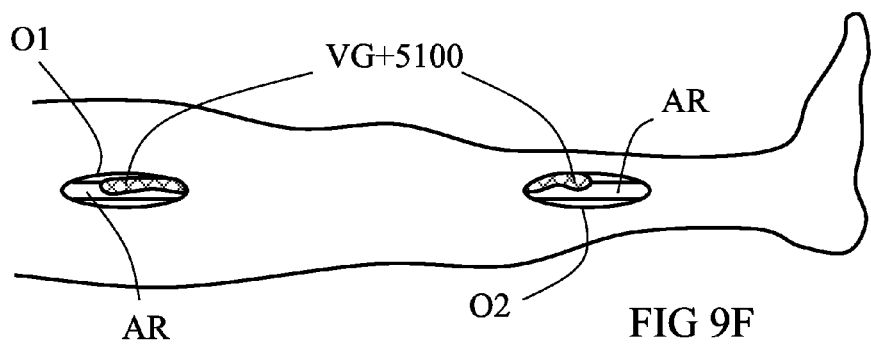
FIG 9F

EXTERNAL SUPPORT FOR ELONGATED BODILY VESSELS

RELATED APPLICATIONS

This application is a National Phase of PCT Patent Application No. PCT/IL2012/050121 having International filing date of Apr. 3, 2012, which claims the benefit of priority under 35 USC §119(e) of U.S. Provisional Patent Application No. 61/476,347 filed on Apr. 18, 2011. The contents of the above applications are all incorporated herein by reference in their entirety, as if fully set forth herein.

FIELD AND BACKGROUND OF THE INVENTION

The present invention, in some embodiments thereof, relates to mechanical supports for bodily vessels, and in particular to external supports for elongated blood vessels such as peripheral or coronary arterial bypasses grafts.

Arterial occlusive disease, most commonly atherosclerosis, underlies most peripheral arterial disease. Most of the atherosclerotic blockages are found in the lower extremity. As vessel narrowing increases, critical limb ischemia (CLI) can develop when the blood flow does not meet the metabolic demands of tissue at rest. While CLI may be due to an acute condition such as an embolus or thrombosis, most cases are the progressive result of a chronic condition, most commonly atherosclerosis.

A peripheral vascular bypass, also called a lower extremity bypass, is the surgical rerouting of blood flow around an obstructed artery that supplies blood to the legs and feet. The three common peripheral vascular bypass surgeries are aortobifemoral bypass surgery, which reroutes blood from the abdominal aorta to the two femoral arteries in the groin; femoropopliteal bypass surgery, which reroutes blood from the femoral artery to the popliteal arteries above or below the knee and femorotibial bypass surgery, which reroutes blood between the femoral artery and the tibial artery. A substitute vessel or graft must be used in bypass surgeries to reroute the blood. The graft may be a healthy segment of the patient's own saphenous vein (autogenous graft), a vein that runs the entire length of the thigh. A synthetic graft may be used if the patient's saphenous vein is not healthy or long enough, or if the vessel to be bypassed is a larger artery that cannot be replaced by a smaller vein.

In recent years, angioplasty has supplanted peripheral bypass surgery as the first-line therapy for patients with CLI. Endovascular revascularization has become acceptable as a minimally invasive technique that is associated with low morbidity and mortality, reduced hospital costs, and decreased length of hospitalization. The main tradeoff is shorter durability when compared with the surgical alternative, which is still considered optimal strategy for patients that are capable of withstanding an open surgical procedure, and having life expectancy of over two years.

Intimal hyperplasia and tissue modulation are still considered main cause of vein graft failures in arterial bypass surgeries. These failures are accompanied by significant amounts of disability and limb loss resulting in increased resource utilization for the health care system and in a diminished quality of life for the patient. Veins placed in the arterial circulation as bypass conduits are universally subjected to acute increases in pressure and pulsatile hemodynamics, resulting in acute increases in wall shear and radial stress. Trauma during harvesting, pre-bypass morphological changes, and ischemia reperfusion during the procedure may impact the ability of the vein to adapt to these forces.

Externally supporting the graft with an external device has the potential to reduce wall stress and cyclic stretching of medial and endothelial cells and reduce diameter mismatch between the vein graft and the artery, all of which might be expected to reduce wall thickening. The efficacy of external support to the graft has been studied by several groups over the past few years and the findings from pre-clinical studies demonstrated significant inhibition of neointimal formation, reduction of atherosclerosis plaques and overall graft thickening reduction comparing to non-supported grafts.

Prior publications describing grafts provided with external supports or layers commonly suggest bonding of the external support to selectively cover the graft, optionally by using glue or sutures. Exemplary publications include U.S. Pat. No. 5,755,659 to Zurbrugg and U.S. Pat. No. 7,998,188 to Zilla et al., the disclosures of which are fully incorporated herein by reference. Such grafts may be provided to the medical practitioners readily covered and supported, or that the medical practitioners or their supporting team are instructed to bond the graft and the external support together prior to grafting. The latter scenario may be time consuming and bothersome to the medical team and may derive special training and expertise in materials bonding and preparations so that the finalized artifact will be satisfactory prepared in a timely manner.

International patent application published as WO 2010/058406 to Orion et al., the disclosure of which is fully incorporated herein by reference, describes a plastically deformable external support which further allows shaping and casting of the graft once deployed thereto. The plastic deformity allows the practicing surgeon to shape such external supports to a self-fixating form characterized with a final length, diameter and/or contour, with minimal elasticity and/or spring-back, thereby diminishing the need to use other means to maintain relative positioning and coverage of the graft and the external support.

Further needs stand out when a graft is substantially long, as for example in peripheral bypass surgeries, where it is common to use grafts which are longer than 20 cm and may even extend up to 50 cm, 60 cm and even more. External supports covering long vein grafts in legs and arms, for example, are prone to encounter substantial axial forces, shortening and/or fraying caused by internal radial pressure or by external forces commonly associated with proximity to skin surface and normal function of the limb. Therefore, there is a need to develop external supports also for supporting long grafts, being capable of resisting axially compressing forces while substantially maintaining chosen length, diameter and/or structure while not shifting or displacing from a needed vein graft coverage form, and while obviating the need for external bonding means such as adhesives, clips and sutures.

SUMMARY OF THE INVENTION

In an aspect of some embodiments there is provided an external bodily vessel support that includes an elongate body with a longitudinal axis and an interior to be brought into apposition with an exterior of the bodily vessel.

In some embodiments of the invention, the elongate body including a tubular fabric of a plurality of threads, the body when in a relaxed configuration having a relaxed length and being sized and shaped to fit over of the exterior of the bodily vessel, the tubular fabric being longitudinally elastic to maintain the length with an axial stiffness of at least 0.1 N/m.

Optionally, alternatively or additionally, the elongate body is including a plurality of intertwined threads, the body when in a relaxed configuration having a relaxed length and being sized and shaped to fit over of the exterior of the bodily vessel, the plurality of intertwined threads form an angle with the longitudinal axis being 50° or less at the relaxed configuration.

Optionally, alternatively or additionally, the elongate body is including a plurality of intertwined threads, the body when in a relaxed configuration having a relaxed length and being sized and shaped to fit over of the exterior of the bodily vessel; wherein the relaxed substantially length is greater than a distance between two ends of the bodily vessel when anastomosed and being so chosen as to provide the elongate body in a compressed length, being equal or less than the distance, when placed between the two anastomosed ends to thereby generate an axial preload of at least 0.001 N, optionally at least 0.005 N, optionally at least 0.01 N, optionally at least 0.1 N, or higher, or lower, or intermediate.

In some embodiments, the apposition is provided without curing, bonding, or external fixating means. In some embodiments, the plurality of threads form an angle with the longitudinal axis being 50° or less at the relaxed configuration. In some embodiments, the plurality of threads forms acute angles therebetween at the relaxed configuration.

In some embodiments, the bodily vessel is a long vein graft.

In some embodiments, the relaxed length is 20 cm or more.

In some embodiments, the plurality of threads is made of a Cobalt-Chromium alloy.

In some embodiments, the elongate body being configured to extend up to 110% the length at a full radial crush thereof.

In some embodiments, the elongate body is radially and axially elastic.

In an aspect of some other embodiments of the present invention, there is provided an external bodily vessel support which includes an elongate body with a longitudinal axis and an interior to be brought into apposition with an exterior of the bodily vessel, the elongate body including a tubular fabric having intertwined coiled compression springs.

In some embodiments, the intertwined coiled compression springs having a first set of first compression springs and a second set of second compression springs of a larger spring constant than of the first compression springs. In some exemplary embodiments, the larger spring constant is at least 0.05 N/m and/or a smaller spring constant of the first compression springs is at most 0.035 N/m.

In some embodiments, the first set includes at least twenty of the first compression springs and the second set includes at most ten of the second compression springs.

In some embodiments, the quantity ratio between the first set and the second set is equal or greater than 8.

In some embodiments, the first coiled compression springs are 75 μm or less in diameter and the second compression springs are 75 μm or more in diameter.

In some embodiments, the first coiled compression springs are 50 μm or less in diameter and the second compression springs are 50 μm or more in diameter.

In some embodiments, the intertwined coiled compression springs are made of a Cobalt-Chromium alloy.

In some embodiments, the elongate body is provided in a compressed length confined by an external deployment device. In some embodiments, the external deployment device is selectively extendable to any fixed length greater than a minimal compressed length of the elongate body and smaller than a relaxed length of the elongate body.

In an aspect of some other embodiments of the present invention, there is provided a kit for providing an external support to a bodily vessel, which includes an external bodily vessel support of the present invention for providing external support to a bodily vessel, and a delivery device for placing the external tubular support over the bodily vessel, the delivery device includes an internal passage of at least 6 mm in diameter and outer dimensions sized to alter the external bodily vessel support to a compressed form.

In some embodiments, the compressed form includes a compressed length being 70% or less the relaxed length and/or an expanded diameter being 30% or more a relaxed diameter of the external bodily vessel support being at the relaxed configuration. In some embodiments, the tubular support being pre-loaded onto the delivery device.

In some embodiments, the kit further includes threading means for threading a bodily vessel having a first end and a second end through the passage.

In an aspect of some other embodiments of the present invention, there is provided a method of implanting a peripheral graft, the method includes:

drawing an external bodily vessel support, having a relaxed length and being sized and shaped to fit over of an exterior of the bodily vessel, over a delivery device includes an internal passage of at least 6 mm in diameter, including compressing the external bodily vessel support from the relaxed length to a compressed length;

threading a bodily vessel having a first end and a second end through the passage;

externally supporting the bodily vessel by unloading the external bodily vessel support from the delivery device along the bodily vessel and into apposition therewith while regaining the relaxed configuration; and extending the externally supported body vessel across a superficial percutaneous tunnel.

In some embodiments, the threading is performed after anastomosing the first end.

In some embodiments, the threading includes: connecting threading means to the second end; pulling the threading means; and passing the delivery device over the threading means to reach the first end.

In some embodiments, the superficial percutaneous tunnel is enclosed with a tunneler readily provided between surgical made openings.

In some embodiments, the extending includes: connecting threading means, provided in and along the superficial percutaneous tunnel, to the second end; and withdrawing the threading means from the superficial percutaneous tunnel.

In some embodiments, the method includes cutting the external bodily vessel support to the relaxed length being equal or greater than a final size of the bodily vessel.

In some embodiments, the superficial percutaneous tunnel is made in a limb.

In some embodiments, the extending is followed by anastomosing the second end.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 schematically illustrates an externally supported graft as a peripheral arterial bypass, in accordance with embodiments of the present invention;

FIG. 2A-D schematically illustrate cut views at different stages in preparation and deployment of an externally supported vein graft, in accordance with embodiments of the present invention;

FIGS. 9A-F schematically illustrate steps in exemplary method of implanting a vein graft and an external support using tunneling means, in accordance with embodiments of the present invention.

DESCRIPTION OF EMBODIMENTS OF THE INVENTION

Figure 3A:
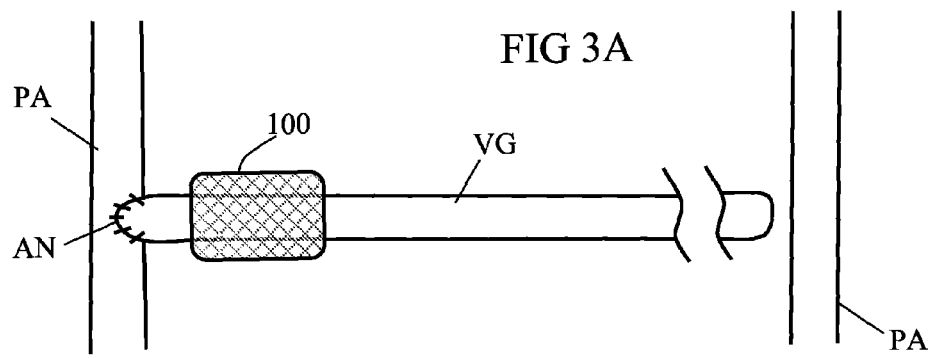
FIGS. 3A-C schematically illustrates exemplary deployment stages of an external support over a graft, in accordance with embodiments of the present invention.

It is understood that the invention is not limited to the particular methodology, described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The term "patient" as in treatment of "a patient" refers to a mammalian individual afflicted with or prone to a condition, disease or disorder as specified herein, and includes both humans and animals.

The term "bodily vessel", unless otherwise defined, refers to blood vessels and grafts, such as veins, arteries and synthetic blood vessels, or a combination of a native vein with a synthetic graft (Such as miller cuff in which the a native vein is being used as the distal part of a synthetic graft to enable a better mechanical match between the vein and the artery), but in some instances may refer to any internal organ, live or synthetic, functioning as a conduit for fluids or other flowable materials in a patient's body.

The terms "graft" and "grafting" refer to a natural or artificial conduit to carry blood between two arteries, and the placement thereof, respectively, for treatment of an arterial stenosis, thrombosis or embolus. It can also refer to the placement of an artificial conduit between an artery and vein of the forearm for use in hemodialysis. Grafts can be used for the aorta (coronary bypass grafts), femoral artery or in the forearm (peripheral bypass grafts). Often, the saphenous vein or left internal thoracic artery are harvested from the patient and used as grafts. PTFE and Dacron are common materials for synthetic vascular grafts.

The term "tissue modulation" refers to any volumetric change in a bodily vessel, such as a graft, as an outcome of tissue grow or hyperplasia, due to internal stresses that are abnormal with respect to the original stresses, pressures and/or flow properties of the bodily vessel. For example, a vein graft placed in an arterial vascular system will be subjected to pressures and internal stresses that are much higher than in a venous vascular system, therefore resulting in intimal hyperplasia, wall thickening, and other tissue modulation outcomes as well as mechanical deformations such as kinking, twisting and/or radially expanding.

The term "external support" or "external bodily vessel support" refers to any device placed over an outside surface of a bodily vessel in order to change some of its geometrical and/or mechanical properties and durability and/or to prevent, lessen and/or positively influence chances of failure, modification and/or tissue modulation thereof, and/or to cast and/or impose a requested shape, size, contour and/or other external boundaries of the bodily vessel. External supports may be in the form of stents or sleeves, and may include fabric, either woven, non-woven, or mechanically machined, and may be made from any materials or elements such as plastics, metals, textiles and others.

The terms "cast", "casting" or "molding" refer to the forming of externally shaped boundaries, optionally three-dimensional, to an externally supported bodily vessel either by constricting and/or changing the vessel shape and/or contour by exerting forces thereto, and/or by restricting its deformation and/or modulation to a specific final shape and/or contour.

The term "fabric" refers to any artifact made by braiding or weaving or felting or knitting or crocheting threads. The term "thread" or "threads" refers to any long structural member resembling a thin line, and may include a wire, including a metal wire, a strand, a yarn, a fiber and other types known to art, natural or synthetic.

The terms "braid" or "braided interlacement" refer to pattern formed by intertwining three or more strands of flexible material, such as wires, threads or yarns, which may be made for example of polymers, textiles or metal (e.g., stainless steel threads). Unless otherwise specified, a braided external support will be referred generally to as ones which include a tubular sheath made of braided threads.

The term "braid angle" or "braiding angle" refers to an angle formed between each two intertwined threads in longitudinal direction of the braid. A braiding angle as defined in the present invention is twice the angle formed between an intertwined thread and the longitudinal direction of the braid. The braiding angle of each thread and/or the average braiding angle of a whole braided external support is changeable depending on state of compression or extension with respect to the braid relaxed length, so unless otherwise defined, a braiding angle of a braided external support shall refer to the braiding angle when in relaxed length.

The term "relaxed configuration" refers to the shape and mechanical properties of the external support when under no internal or external forces, stresses or strains. A relaxed configuration of a braided external support may optionally be determined according to setting considerations such as a mandrel dimensions relative to a metal braid and threads dimensions, and braiding angle of the braid when worn over the mandrel during stress relieving treatments, for example annealing or other heat treatments.

The term "relaxed length" refers to a length of the external support when in relaxed configuration, and when no internal forces, stresses or strains acting to change its length. For example, a longitudinally elastic external support will develop internal stresses which will act to regain a relaxed length when compressed to a shorter length or extended to a longer length than said relaxed length. The term "compressed length" refers to a length shorter than the relaxed length in which the external support has internal stresses acting towards extending its length.

The term "axial stiffness" refers to the resistance of an elastic external support to deformation by a force applied to it in parallel to its longitudinal axis. Unless otherwise defined, axial stiffness shall be considered as a "longitudinal stiffness" that is focused to resistance to contracting the external support from a relaxed length, optionally indicative in a smaller diameter, to a compressed length, optionally indicative in a larger diameter. The axial stiffness of a whole braided external support may be determined by combined elastic properties of its threads (including but not limited to at least one of thread material, thread diameter, thread elastic or plastic properties) and/or the braiding properties (including but not limited to at least one of braiding angle, total number of threads, different threads types and numbers of each).

A thread may be considered a "spring" when it is formed of a spring metal and conditioned to return to its shape and size at relaxed configuration when external compressing or stretching forces cease. A number or spring type threads may be intertwined together and/or with other thread types to create a braided fabric. A spring type thread may be considered a "coiled spring" when it is formed in a spiral or helical wounding to a tubular shape at a relaxed configuration. A "coiled compression spring" refers to an open-coil helical spring that offers resistance to a compressive force applied axially. The coiled compression spring can be compressed up to a minimal length when its entire coils are in full contact therebetween. A "spring constant" shall refer to a characteristic of a spring which is defined as the ratio of the force affecting the spring to the displacement caused by it as long as the load does not exceed the material's elastic limit. Whereas stiffness relates to the elastic properties of the whole external support, the spring constant relates to the elastic properties of a single spring member such as a spring type thread.

The terms "elastic" or "elastically deformable" refer to being capable of resuming original shape after stretching or compression. The term "plastic" or "plastically deformable" refer to a pliant member being capable of substantially maintaining a chosen shape it has been formed to. A plastically deformable member, for example a thread, a fabric or an entire external support, is readily provided soft and ductile and fixedly stretchable and/or shapeable to chosen formation until less than a fracture point and therefore conditioned to be selectively shift from a first relaxed configuration to a second relaxed configuration.

The term "preload" refers to a force continuously exerted by a spring being held in a compressed length. The preload shall equal substantially the external support axial stiffness multiplied by the difference between its relaxed length and its current compressed length. For example, when elastic and/or a spring-type external support is being compressed, for example if held compressed over an implanted graft being of a length (e.g., distance between two anastomosed ends) that is substantially smaller than the relaxed length of the external support. If preloaded, the external support of the present invention exerts the preload towards both anastomosed ends of the supported graft, therefore improve axial stability and/or fixation to the graft without a use of any bonding, curing and/or suturing means.

The following preferred embodiments may be described in the context of exemplary vascular bypass procedures for ease of description and understanding. However, the invention is not limited to the specifically described devices and methods, and may be adapted to various clinical applications without departing from the overall scope of the invention. For example, devices and related methods including concepts described herein may be used for externally supporting grafts and other bodily vessels such as but not limited to: arteries, veins, synthetic grafts, coronary bypass grafts, peripheral bypass grafts, gastrointestinal vessels, and soft and semi-hard tissues.

The present invention, in some embodiments thereof, relates to mechanical supports for bodily vessels, and in particular to external supports for long blood vessels such as peripheral blood vessels or grafts.

In an aspect of some embodiments there is provided an external bodily vessel support comprising an elongate body with a longitudinal axis and an interior to be brought into apposition with an exterior of the bodily vessel. In some embodiments, the apposition is provided without curing, bonding, or external fixating means. The bodily vessel may be a blood vessel, coronary or peripheral, venous or arterial, native or graft. In case of a graft, the appositioning may be performed before the graft is implanted, during implantation (e.g., when only one end of the graft is anastomosed) or after the graft is implanted (i.e., when both ends thereof are anastomosed and blood is allowed to flow therethrough). In some embodiments, the elongate body, at apposition with the exterior of the bodily vessel, it supports the bodily vessel, and optionally imposes and/or casts a requested longitudinal shape along the bodily vessel length, for example when there is a need to fortify a vein graft to better suit increased pressures and flow regimes such that of the target vascular system, usually an arterial system.

In some embodiments of the invention, the elongate body includes a tubular fabric of a plurality of threads and is characterized by having a relaxed configuration. In some embodiments, the fabric includes a braid and/or is a braid, optionally a tubular braid. Optionally, alternatively or additionally, the fabric includes weaving or knitting. Optionally, the body, when in its relaxed configuration, has a relaxed length and is being sized and shaped to fit over of the exterior of the bodily vessel.

In some exemplary embodiments, the plurality of threads includes coiled compression springs. Optionally, the tubular fabric comprises a braid and said coiled compression springs are intertwined to form the braid. Optionally, the coiled compression springs include a first coiled spring having a first spring constant being larger than a second spring constant of a second coiled spring thereof. In some exemplary embodiments, a first spring constant is optionally at least 0.001 N/m, optionally at least 0.01 N/m, optionally between 0.015 N/m and 0.035 N/m, or higher or lower or intermediate, whereas a second spring constant is optionally at least 0.05 N/m, optionally at least 0.1 N/m, optionally between 0.08 N/m and 0.2 N/m, or higher, or lower, or intermediate. In some embodiments, the first and/or second spring constant is configured parallel to the longitudinal axis of the elongate body.

In some embodiments of the invention, the tubular fabric is longitudinally elastic to maintain the relaxed length with an axial stiffness, optionally at least 0.1 N/m, optionally at least 0.5 N/m, optionally at least 1 N/m, optionally at least 2 N/m, or higher, or lower or intermediate. In some embodiments, the tubular fabric is longitudinally elastic to resist axial compression thereof. Optionally, the tubular fabric is also radially elastic to maintain a tubular shape thereof.

In some embodiments of the invention, the fabric is a metal fabric, and optionally at least a portion of the threads are made of metal, such as a metal alloy, optionally Cobalt-Chromium alloy.

In some embodiments, two threads or more, optionally the plurality of threads, form a braiding angle being 100° or less, optionally in the range 40°-100°, at relaxed configuration, optionally acute angles, optionally in the range 50°-90°. Optionally, the plurality of threads form an angle with the longitudinal axis being 50° or less at said relaxed configuration, optionally 40° or less, optionally 30° or intermediate.

In some embodiments, the relaxed length of the elongate body is 5 cm or more, optionally 10 cm or more, optionally 20 cm or more, optionally 50 cm or more, optionally 20 to 90 cm. In some embodiments, the relaxed length substantially equals a distance between two ends of said bodily vessel when anastomosed. Alternatively, the relaxed length is larger than a distance between two ends of said bodily vessel when anastomosed. In some embodiments, the relaxed length is so chosen as to compress said elongate body to a compressed length when placed between said two anastomosed ends with an axial preload of at least 0.001 N, optionally at least 0.005 N, optionally at least 0.01 N, or higher, or lower, or intermediate.

In some embodiments, the elongate body is radially and axially elastic. In some embodiments of the invention, the elongate body is configured to extend up to 120% its relaxed length, optionally up to 110%, optionally up to 105%, when at a full radial crush. Optionally, alternatively or additionally, the elongate body or fabric comprises a plastically deformable thread. Optionally, alternatively or additionally, the elongate body or fabric comprises at least one elastic thread that is adapted to pass yield point when extended over a predetermined length that is equal or less than said elongate body relaxed length.

In some embodiments, the elongate body is provided in a compressed length confined by an external deployment device. Optionally, the external deployment device is selectively extendable to any fixed length greater than a minimal compressed length of and smaller than a relaxed length of the elongate body.

In an aspect of some embodiments there is provided an external bodily vessel support comprising an elongate body with a longitudinal axis and an interior to be brought into apposition with an exterior of said bodily vessel, the elongate body including a tubular fabric having intertwined coiled compression springs. In some embodiments of the invention, the intertwined coiled compression springs having a first set of first compression springs and a second set of second compression springs of a larger spring constant than of said first compression springs. In some embodiments, the first set includes at least twenty, optionally at least 30, of said first compression springs and the second set includes at most ten, optionally at most 5, of the second compression springs. In some embodiments, the quantity ratio between the first set and the second set is equal or greater than 6, optionally equal or greater than 8, optionally equal or greater than 10, or higher or lower or intermediate. In an exemplary embodiment, the elongate body includes evenly spaced intertwined coiled compression springs including 38 threads, each thread having a smaller spring constant of approximately 0.01-0.03 N/m, and 4 threads, each thread having a larger spring constant of approximately 0.05-0.15 N/m. In an exemplary embodiment, the two threads types are substantially similar in material and condition but optionally differ substantially in diameter. In some embodiments, the first coiled compression springs are 75 μm or less in diameter and the second compression springs are 75 μm or more in diameter. Optionally, alternatively or additionally, the first coiled compression springs are 50 μm or less in diameter and the second compression springs are 50 μm or more in diameter. In an exemplary embodiment, the first coiled compression springs are approximately 50 μm and the second compression springs are approximately 75 μm in diameter. In some embodiments, all intertwined coiled compression springs are made of a Cobalt-Chromium alloy.

In to an aspect of some other embodiments of the present invention there is provided an external bodily vessel support for use with an elongate graft to facilitate a desired external casting boundary for tissue modulation when the elongate graft is grafted into a vascular system. According to some embodiments of the present invention, the external bodily vessel support includes an elongate body having a first end and a second end with a channel therebetween sized to fit over a maximal diameter of the elongate graft, the elongate body is adapted to axially extend from a first compressed length to a second relaxed length. In some embodiments, the bodily vessel support further includes a structural member extending at least partially along the elongate body and adapted to suppress axial compression when in the relaxed length. In some embodiments, the elongate graft is a vein graft. Optionally, the vascular system is an arterial vascular system.

In some embodiments, the elongate body includes a meshed sleeve formed of intertwined threads. In some embodiments, the meshed sleeve includes a braided interlacement. In some embodiments, the braided interlacement includes braiding angle of less than 100°, optionally less than 60°, when the elongate body is in the second relaxed length.

In some embodiments, the elongate body and/or structural member has an axial stiffness of at least 0.01 N/m, optionally at least 0.1 N/m when in the second relaxed length.

In some embodiments, the elongate body decreases in diameter when extending from the first compressed length to the second relaxed length by at least 20%, optionally by at least 50%. In some embodiments, the elongate body increases in length when extending from the first compressed length to the second relaxed length by at least 100%, optionally by at least 500%.

In some embodiments, the elongate body is self-extendable from the first compressed length to the second relaxed length. Optionally, the elongate body is radially and/or axially elastic. Optionally, the bodily vessel support includes a plastically deformable thread. In some embodiments, the bodily vessel support includes at least one elastic thread adapted to pass yield point when extended over a predetermined length that is equal or less than the elongate body relaxed length.

In some embodiments, the relaxed length of the elongate body is substantially equal or greater than a length of the elongate graft when grafted into the vascular system. Optionally, the relaxed length of the elongate body is substantially equal or greater than 20 cm. Optionally, the compressed length of the elongate body is substantially equal or lesser than 15 cm.

In some embodiments, the desired external casting boundary includes at least one of a tapered tubular shape and a cylindrical shape.

In some embodiments, the elongate body comprises a meshed portion extendable from the axially compressed form to an axially extended form. In some embodiments, the meshed portion is braided and is characterized by decreasing in diameter when extending. In some embodiments, the elongate body is shrinkable to fit in diameter to a graft having maximal and minimal outer diameters in between 3 to 9 mm.

Referring to the figures, FIG. 1 schematically illustrates an externally supported graft 100 utilized as a peripheral arterial bypass connected over an obstructed portion of a peripheral artery PA in a patient's extremity or limb (in this example a leg) LMB. FIGS. 2A-D schematically illustrate cut views of a portion of external support 100 at different stages of preparation and deployment, in accordance with embodiments of the present invention.

FIGS. 2A and 2D respectively present original and requested forms of a portion of an exemplary saphenous vein graft SV, presented herein as an exemplary bodily vessel in need for external support, before harvesting and after grafting in a peripheral arterial system, such as the arterial system comprising peripheral artery of PA of FIG. 1. As shown in FIG. 2A, vein portion SV decreases in diameter from a diameter Dp1 at its proximal to end diameter Dd1 at its distal end in view of the need to sustain certain blood flow and pressure ranges when the blood flows from patient's (or donor's) limb to its heart. A second aspect of consideration is the presence and orientation of a plurality of venous valves VV positioned along vein portion SV which can only allow a unidirectional flow from distal end (limb) to proximal end (heart). A third aspect of consideration is the thickness T1 and mechanical and anatomical properties of vein portion SV wall which are directly linked with its durability and functionality in certain internal pressures and flow regimes. The requested graft form as shown in FIG. 2D includes changes in all three aspects (and optionally others not specified above) including maintaining a diameter decrease from proximal end (heart) to distal end (limb) while optionally enlarging the diameters from Dp1 to Dp2 and/or Dd1 to Dd2; setting the graft in a reversed position so that its venous valves VV will allow unidirectional flow from heart to limb; and modified wall having improved mechanical properties and durability with optional thickening from T1 to T2.

As a preliminary non-binding step, a portion of a saphenous graft SV, previously harvested from the patient or from a donor, is prepared for grafting in an arterial system, in this example a peripheral arterial system, where it is checked for possible leakages to seal and optionally and/or partially cleaned from collaterals outwardly projecting along its length. During or after preparation of vein graft VG it is anastomosed in one end to an artery. Alternatively, an arterial harvested graft or a synthetic graft is used instead.

As shown in FIG. 2B, vein graft VG is repositioned when grafted to allow an opposite unidirectional flow in a distal direction (from the heart towards the extremities). Then, external support 100 is placed (FIG. 2C) to extend over graft VG substantially along its entire length. In some embodiments, at a final relaxed length, external support 100 maintains a final shape allowing casting of a remodeling vein graft to more homogenous outer boundaries, optionally to final shape and boundaries as shown in FIG. 2D.

Figure 3B:
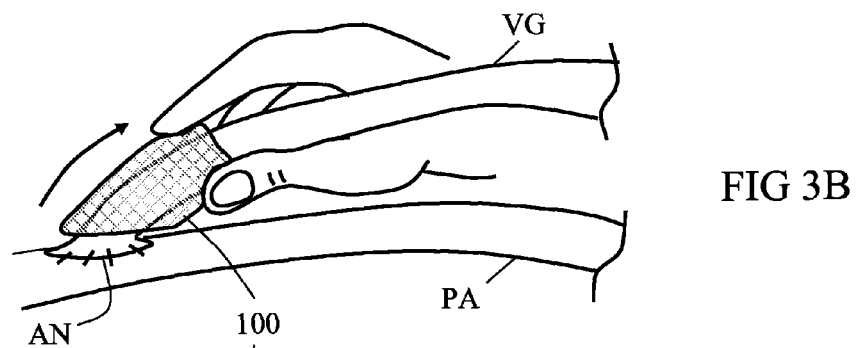
Figure 3C:
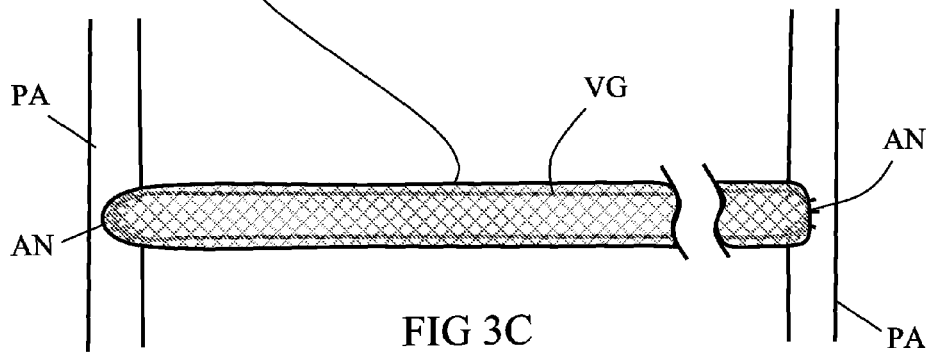

FIGS. 3A-C schematically illustrate exemplary deployment stages of external support 100 over vein graft VG previously connected at one end thereof to peripheral artery PA by anastomosis AN, in accordance with embodiments of the present invention. Main stages of external support 100 deployment includes its positioning distally or proximally along the length of vein graft VG and then extending it, manually or otherwise, until covering most or all of vein graft length. Such extension may be performed before or after connecting the free end of vein graft VG to a second distant location along peripheral artery PA. Optionally, the extended external support 100 covers at least one of the anastomosed areas AN. In some embodiments, both anastomosed areas are covered with external support 100, as shown in FIG. 3C, which may also include tapered portions at one or both its ends. Optionally, alternatively or additionally, external support 100 has a relaxed length which is substantially greater than graft VG length and/or the distance between the two anastomosed ends, so that in it is being compressed to substantially less its relaxed length. Optionally, in such a scenario, external support 100 generates an axial preload of at least 0.001 N, optionally at least 0.005 N, optionally at least 0.01 N, optionally at least 0.1 N, or higher, or lower, or intermediate.

In some embodiments, external support 100 is adapted to axially extend from a first compressed length to a second relaxed length. External support 100 is optionally placed over or sleeved over vein graft VG while in a compressed length thereby easing its handling and positioning. External support 100 may include internal/structural means to hold it in the compressed length or it may be deployed with a delivery device or other deployment means which facilitate this feature. Optionally, alternatively or additionally, a chosen patterned design, for example a braiding including a plurality of intertwined wires optionally of different diameters and/or materials and/or conditions, optionally at chosen braiding angles, determines its axial stiffness and resistance to axial deformation (e.g., contraction). In some embodiments, external support 100 is deployed when in substantially larger diameter than of vein graft VG so it can be easily slipped thereto. In some embodiments, compressing external support 100 enlarges its diameter and vice versa.

In some embodiments, external support 100 increases in length when extending from a first compressed length to a final covering length, optionally a relaxed length, by at least 50%, optionally by at least 100%, optionally by at least 400%, optionally by at least 1,000%, optionally between 200% and 400%. Optionally, external support 100 is deployed in a compressed length of less than 300 mm, optionally less than 100 mm, optionally less than 50 mm, optionally less than 15 mm, or higher, or lower or in any intermediate length. Optionally, external support 100 is adapted to extend to a chosen length, optionally a relaxed length, which is at least 50 mm, optionally at least 100 mm, optionally at least 400 mm, optionally at least 600 mm, or higher, or lower or any intermediate value.

In some embodiments of the present invention, external support 100 is provided having internal diameter substantially larger than in its in relaxed length, optionally more than 50% its relaxed length diameter, optionally more than 100%, optionally more than 150%, optionally more than 200%, optionally 130% to 180% (for example, when compressed to a length of 30%-40% its relaxed length), or higher, or lower, or intermediate. In some embodiments, external support 100 decreases in diameter when extending from a first compressed length to a final covering length, optionally a relaxed length, by at least 20% optionally at least 60%, optionally between 30% and 50%. Optionally, external support 100 is deployed in a minimal diameter larger than 5 mm, optionally larger than 10 mm, optionally larger than 30 mm, or higher, or lower or in any intermediate diameter. Optionally, external support 100 is adapted to decrease in diameter, optionally to less than 10 mm, optionally to less than 5 mm, optionally to less than 3 mm, optionally between 4 mm to 6 mm, optionally between 4.2 mm to 5.6 mm, when in relaxed length, or higher, or lower or to any intermediate value.

In some embodiments, when extended, the external support 100 substantially maintains its extended length. Optionally, this characteristic makes redundant the need to fasten or glue it to the graft, the arteries or to the anastomosed areas, as practiced in deployments of other known devices, such as the "eSVS™ mesh" for coronary artery bypass grafting ("Kips Bay Medical Inc.", MN, USA) or as previously disclosed in U.S. Pat. No. 5,645,581 to Zurbrugg. In some embodiments, external support 100 is designed for a maximally allowed axial expansion at extreme scenarios. Due to the superficial course of the vein graft, for example when grafted in the leg, it may undergo focal and diffuse radial contractions (e.g., spasms, pinches or "crushes") due to pressure from the external environment (for example when the patient seats, sleeps or when the graft is pressed from some reason). If such crushes will cause substantial elongations to the support over the vein graft, this may endanger the vein graft or even cause the graft to (e.g., due to friction). In some exemplary embodiments of the invention, in case of a full crush (i.e., internal diameter of external support 100 substantially zeroes), the maximal elongation of external support 100 does not exceed 1% its relaxed length, optionally 5%, optionally 10%, or higher, or lower, or intermediate.

Optionally, an axial stiffness or a non-recompressing feature is applicable only when external support 100 is stretched over a predetermined minimal length. Alternatively or additionally, external support 100 includes elastic properties and the non-recompressing feature is applicable when it is stretched or left to extend to or over its relaxed length. Optionally, external support 100 is radially and/or axially elastic. In some embodiments, external support 100 is self-extendable from a first compressed length to a second relaxed length. In some embodiments, external support 100 further comprises a structural member extending at least partially along said elongate body and adapted to suppress axial compression when in said relaxed length. In some embodiments, external support 100 or any structural member thereof has an axial stiffness of at least 0.01 N/m when in the relaxed length, optionally at least 0.1 N/m, optionally at least 1 N/m, optionally at least 2 N/m, optionally at least 5 N/m, or higher, or lower, or any intermediate value.

In some embodiments, at least a portion of external support 100 in its final, optionally relaxed, length shrinks-to-fit and/or takes the form of the already grafted and functioning vein graft VG. Alternatively or additionally, at least a portion of external support 100 constrict graft VG to smaller dimensions thereby increasing its passive resistance to internal pressures. Alternatively or additionally, at least a portion of external support 100 maintains a chosen tubular shape that may be smaller, equal and/or larger in diameter than portions of graft VG along its length, thereby restricting its expansion and/or any deformation, cell growth and/or tissue modulation to the chosen shape boundaries. In some embodiments, a desired external casting boundary includes at least one of a tapered (or partially conic, as shown in FIG. 2C) tubular shape and a cylindrical shape.

Figure 4:
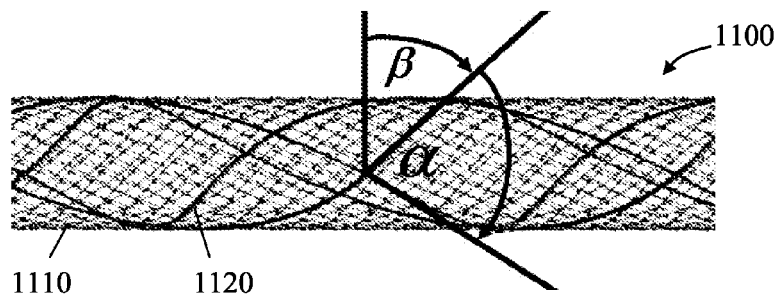
FIG. 4 illustrates a portion of an exemplary braided external support, in accordance with embodiments of the present invention.

Reference is now made to FIG. 4 which illustrates a portion of an exemplary external support 1100, in accordance with embodiments of the present invention. In some embodiments, external support 1100 includes a meshed sleeve formed of interlaced threads, optionally a braided interlacement. In some embodiments, external support 1100 includes at least one type of threads or wires, for example wires 1110 and 1120 which may be differentiated by at least one of quantity, material, conditioning, dimension (e.g., diameter), mechanical processing, chemical processing, covering with other material (e.g., silicon), or others. In one example, wires 1110 are elastically deformable (i.e., resumes a relaxed form and/or length when stretched until less than a yield point), whereas wires 1120 are plastically deformable at in-body conditions. Alternatively, both wire types are elastic. In some embodiments, all wires are provided in mechanical properties applicable for easy cutting, scissoring and/or shearing, optionally by surgical scissors in-site, after initial placement over a vein graft.

In some embodiments, external support 1100 includes metal wires, such as Ni—Ti or Co—Cr alloys. In some embodiments, Cobalt-Chromium alloy ASTM F1058 are used, for both wires 1110 and 1120, being of preferred combination of high strength and stiffness compared to some other implantable metal wires, including Ni—Ti alloys (having lesser stiffness) and common stainless steel (having lesser strength).

Optionally, alternatively or additionally, external support 1100 includes any of the following biocompatible materials provided as wires or in other form: Metals or alloys such as Magnesium, Tantalum, and multiphase alloy; polymers such as PTFE, PET, Nylon, Polyethylene, Polyamide, Polypropylene, Aramid; and biodegradable or bioabsorbable materials such as Magnesium Oxide, Polyglycolide (PGA), Polylactide (PLA), Polycaprolactone, Poly(dioxanone), Poly(lactide-co-glycolide), Ployhydroxybutyrate (PHB) and Ployhydroxyvalerate (PHV). Optionally, at least one wire is provided as a spring type wire that is self-extendable from compressed length to a relaxed length.

In some embodiments, external support 1100 includes at least 10 wires, optionally at least 20 wires, optionally at least 60 wires, or more, or less, or intermediate. In some embodiments, at least one wire includes a diameter that is equal or greater than 10 μm, optionally equal or greater than 25 μm, optionally equal or greater than 75 μm, optionally equal or greater than 100 μm, optionally equal or greater than 125 μm, or higher, or lower, or intermediate.

In some embodiments, external support 1100 includes threads or wires 1110 and/or 1120 that are braided in a braiding angle α, at relaxed length, that is equal or less than 100°, optionally equal or less than 90°, optionally equal or less than 60°, optionally between 20° to 90°. In some embodiments, braiding angle varies along a length of external support 1100 and/or is different in portions thereof. In some embodiments, as for example in case where an external support is braided over a non-cylindrical mandrel (e.g., a conic shaped mandrel), braiding angle varies along the length in order to have specific chosen characteristics of the external support. In the last example, braiding angle α will be considered as the average braiding angle of external support 1100.

In some exemplary embodiments of the invention, the braiding angle of external support 1100 is less than 100° in relaxed length. In some embodiments, the low braiding angle allows a substantial increase (e.g., over 20%) in diameter thus enabling threading of the device on the vein graft without damaging the side branches/clips. Optionally, alternatively or additionally, the low braiding angle provides substantial longitudinal or axial stiffness, optionally over 0.5 N/m, optionally over 1 N/m. In some exemplary embodiments of the invention, wires diameters are chosen between 30 μm and 100 μm. In some embodiments, wires 1110 and 1120 differ in diameters and numbers: wires 1110 having smaller diameters (e.g., 30-50 μm) but provided in larger amount (e.g., 20 to 50 units), being mostly influential to overall support mesh properties, softness and function under high radial forces, and wires 1120 having larger diameters (e.g., 75-100 μm) but in smaller numbers (e.g., 2 to 5 units), being mostly influential to overall support axial stiffness.

The following tables present some exemplary embodiments for external support 1100 and/or external support 100, (made from Co—Cr wires, ASTM 1058). All data is the product of mathematical calculations based on a mathematical model specifically developed for self-expanding metallic braided stents, taken from Jedwab et al. (1993) "A study of geometrical and mechanical properties of a self-expanding metallic stent—theory and experiment", Journal of Applied Biomaterials, Vol. 4, 77-85, the disclosure of which is fully incorporated herein by reference.

TABLE 1

Exemplary properties of external support comprising single wire type

| Wires diameter [μm] | Number of Wires | Internal Diameter [mm] | Length [mm] | Braiding angle [Deg] | Axial Force [N] | axial stiffness [N/m] | radial pressure [N/m2] | Maximal Diameter [mm] | Minimal Length [mm] | Length reduction [%] |
|---|---|---|---|---|---|---|---|---|---|---|
| 25 | 24 | 7 | 600 | 90 | 3.78E−05 | 0.010159 | 0.477799 | 9.9 | 100.48 | 83.25 |
|  |  |  |  | 55 | 1.55E−05 | 0.0147379 | 0.053673 | 15.2 | 63.77 | 89.37 |
|  |  |  |  | 20 | 2.28E−06 | 0.017776 | 0.000909 | 40.5 | 42.58 | 92.90 |
|  |  | 6 | 500 | 90 | 5.99E−05 | 0.0166286 | 1.025336 | 8.55 | 26.35 | 94.73 |
|  |  |  |  | 55 | 2.46E−05 | 0.0241088 | 0.115401 | 13.1 | 10.60 | 97.88 |
|  |  |  |  | 20 | 3.62E−06 | 0.0290697 | 0.001955 | 34.8 | 24.48 | 95.10 |
|  |  | 5 | 400 | 90 | 0.000103 | 0.030021 | 2.525973 | 7.1 | 61.06 | 84.73 |
|  |  |  |  | 55 | 4.24E−05 | 0.0434888 | 0.285052 | 10.9 | 36.88 | 90.78 |
|  |  |  |  | 20 | 6.13E−06 | 0.0523896 | 0.004754 | 29 | 30.26 | 92.43 |
|  |  | 4 | 300 | 90 | 0.0002 | 0.062823 | 7.594431 | 5.7 | 41.54 | 86.15 |
|  |  |  |  | 55 | 8.23E−05 | 0.0908921 | 0.860397 | 8.7 | 42.93 | 85.69 |
|  |  |  |  | 20 | 1.21E−05 | 0.1094781 | 0.014601 | 23.3 | 13.55 | 95.48 |
| 43 | 42 | 7 | 600 | 90 | 0.000977 | 0.1569739 | 12.10293 | 10 | 53.85 | 91.02 |
|  |  |  |  | 55 | 0.000401 | 0.2271455 | 1.370494 | 15.3 | 52.33 | 91.28 |
|  |  |  |  | 20 | 5.9E−05 | 0.2736155 | 0.023254 | 40.8 | 10.98 | 98.17 |
|  |  | 6 | 500 | 90 | 0.001545 | 0.2573061 | 25.84322 | 8.6 | 28.29 | 94.34 |
|  |  |  |  | 55 | 0.000635 | 0.3719534 | 2.935662 | 13.1 | 62.13 | 87.57 |
|  |  |  |  | 20 | 9.34E−05 | 0.4478178 | 0.049852 | 35 | 26.52 | 94.69 |
|  |  | 5 | 400 | 90 | 0.002654 | 0.4654523 | 63.2275 | 7.1 | 90.61 | 77.35 |
|  |  |  |  | 55 | 0.001091 | 0.6719047 | 7.213765 | 11 | 22.68 | 94.33 |
|  |  |  |  | 20 | 0.00016 | 0.8083708 | 0.122638 | 29.2 | 31.53 | 92.12 |
|  |  | 4 | 300 | 90 | 0.005138 | 0.9768603 | 188.1593 | 5.7 | 69.37 | 76.88 |
|  |  |  |  | 55 | 0.002114 | 1.4072524 | 21.60593 | 8.8 | 35.31 | 88.23 |
|  |  |  |  | 20 | 0.000311 | 1.6912863 | 0.36793 | 23.5 | 15.28 | 94.91 |

TABLE 2

Exemplary properties of external support comprising two wire types

| Wires number × diameters [μm] | Exemplary properties at relaxed length ||||||| At compressed length α = |
|---|---|---|---|---|---|---|---|---|
| | Internal Diameter [mm] | Length [mm] | Braiding angle [Deg] | Longitudinal stiffness [N/m] | Radial pressure [N/m2] | Maximal Diameter [mm] | Minimal Length [mm] | 150° Final Diameter [%] |
| 4 × 75 μm + 38 × 50 μm | 6.5 | 600 | 90 | 0.467 | 58.9 | 9.03 | 214.8 | 138.9 |
| | | | 70 | 0.589 | 18.6 | 11.12 | 188.3 | 171.1 |
| | 6 | 500 | 90 | 0.659 | 87.1 | 8.34 | 180.8 | 139 |
| | | | 70 | 0.831 | 27.6 | 10.29 | 154.2 | 171.5 |
| | 5.5 | 400 | 90 | 0.983 | 133.1 | 7.65 | 146.4 | 139.1 |
| | | | 70 | 1.239 | 42.3 | 9.45 | 122.7 | 171.8 |
| | 4.6 | 300 | 90 | 1.887 | 317.3 | 6.43 | 107.5 | 139.8 |
| | | | 70 | 2.376 | 101.2 | 7.93 | 92.3 | 172.4 |

Figure 5:
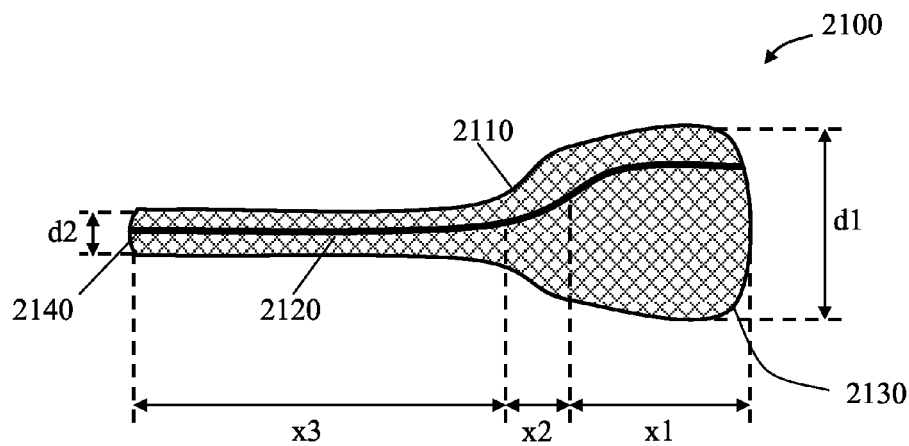
FIG. 5 schematically illustrates an exemplary partially extended braided external support comprising structural deployment assisting means, in accordance with embodiments of the present invention.

Reference is now made to FIG. 5 which schematically illustrates an exemplary partially extended braided external support 2100 having proximal end 2130 and distal end 2140 and a braiding pattern 2110 comprising at least one wire type, preferably made from hardened steel (i.e., incorporating elastic or super elastic properties in body conditions). In some embodiments, external support 2100 is provided in a compressed length deriving an enlarged maximal diameter d1 and is sized and configured to be extended, optionally self-extended, to a relaxed length which derives a final minimal diameter d2.

In some embodiments, external support 2100 includes at least one structural deployment assisting means, for example a longitudinally interlaced wire 2120, which extends between ends 2130 and 2140. In some embodiments, such means allow manipulation of external support 2100 in a compressed length and a selective extension thereof until a chosen length. In some embodiments, longitudinal wire 2120 is provided as an elastic thread that is adapted to pass yield point when extended over a predetermined length that is equal or less than a relaxed length of external support 2100. In some embodiments, once extended over its yield point, wire 2120 suppresses longitudinal shortening of external support 2100 and provides axial stiffness to elastic braiding pattern 2110.

In some embodiments, external support 2100 is adapted to gradually extend, as shown in the partially extended formation shown in FIG. 5, wherein external support 2100 has a compressed proximal portion having a length x1, an intermediate length x2 and a relaxed distal portion having length x3. In some embodiments, wire 2120 in this partially extended formation includes an elastic portion extended along length x1, a deforming portion adjacent yield point extended along length x2, and a plastically deformable non-elastic portion extended along length x3. In some embodiments, elastic portion of wire 2120 resists extension of external support 2100 compressed portion, whereas plastically deformable portion of wire 2120 resists collapsing of external support 2100 relaxed portion. Such a feature may be beneficial for selective and accurate covering of a vein graft, although in a non- or less-reversible manner.

Figure 6:
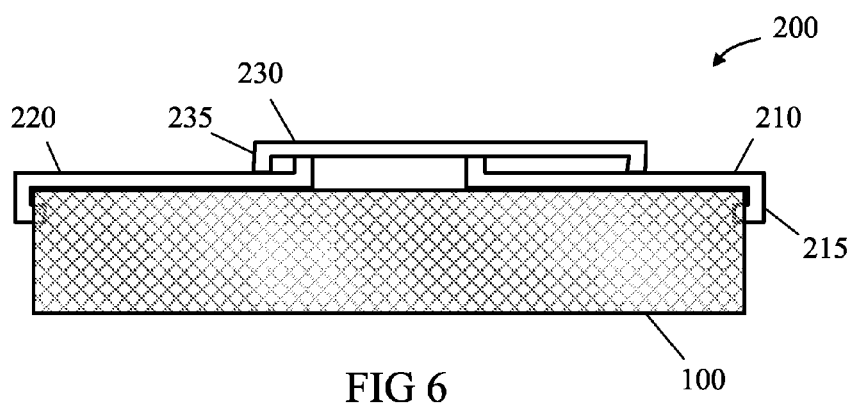
FIG. 6 schematically illustrates an exemplary partially extended braided external support coupled with an exemplary external deployment assisting means, in accordance with embodiments of the present invention.

In some embodiments, an external or appendix mechanism is provided with or in connection with an external support device. Reference is now made to FIG. 6, which schematically illustrates partially extended external support 100 coupled with an exemplary external deployment device, hereinafter referred to as extender 200, in accordance with embodiments of the present invention. In some embodiments, extender 200 is a rail type or a slideably collapsible mechanism comprising at least two members, in this exemplary embodiment three members 210, 220 and 230, which are slideably movable one with respect to the other/s. In some embodiments, extender 200 is axially extendable from a minimal overall length which is at least the length of its lengthiest member, to a maximal overall length when members 210 and 220 are farthest one to the other. In some embodiments, extender 200 includes at least one holder, such as holder 215, which is clingy connectable with an end portion of external support 100. In some embodiments, at least one of members 210, 220 and 230 includes at least one stop, such as stop 235, which is applicable as a limiter for maximal extension of two members, such as members 230 and 220.

In aspects of some embodiments, a kit for surgically supporting an elongated graft may include a delivery device for placing an external tubular support over a chosen length along the graft that is grafted into a vascular system. In some embodiments of the invention, a kit for providing an external support to a bodily vessel comprises an external bodily vessel support, for providing external support to a bodily vessel, and a delivery device for placing the external tubular support over the bodily vessel. In some embodiments, the delivery device comprising an internal passage of at least 6 mm in diameter and outer dimensions sized to alter the external bodily vessel support to a compressed form. In some embodiments, the compressed form includes a compressed length being 70% or less said relaxed length and/or an expanded diameter being 30% or more a relaxed diameter of the external bodily vessel support being at the relaxed configuration. Optionally, the tubular support is pre-loaded onto said delivery device. In some embodiments, the kit further comprising threading means for threading a bodily vessel having a first end and a second end through said passage.

Reference is now made to FIGS. 7A-G which schematically illustrate exemplary stages of preparation and deployment of an external support 3100 over a vein graft VG using an exemplary internal delivery device 300, in accordance with embodiments of the present invention. External support 3100 is braided with a plurality of elastic metal wires, optionally of same type and mechanical properties, optionally made of Ni—Ti alloy. In some embodiments, external support 3100 is tapered or conic-like sleeve shaped having a decreasing cross-section from a first maximal diameter until a second minimal diameter.

In some embodiments, delivery device 300 comprises an elongated body 310 that is a mandrel type device capable of disassembly into at least two parts, such as parts 311 and 312. In some embodiments, the assembled delivery device 300 includes an inner lumen or channel having a minimal diameter Di and is sized to fit over a maximal diameter of a vein graft. The delivery device further includes outer boundaries of changing diameter D(x) that are sized and configured to axially compress at least part of external support 3100 when stretched over it, from an elongated relaxed length to a chosen or predetermined compressed length.

Figure 7A:
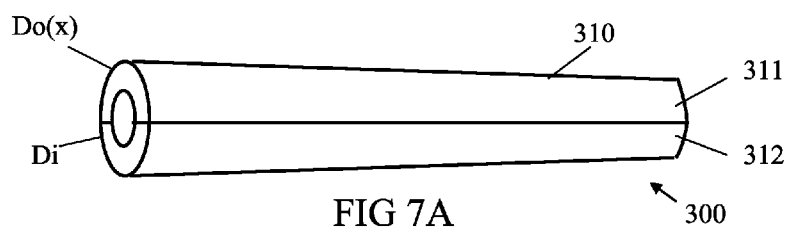
FIGS. 7A-G schematically illustrates exemplary stages of external support preparation and deployment using an exemplary internal delivery device, in accordance with embodiments of the present invention.
Figure 7B:
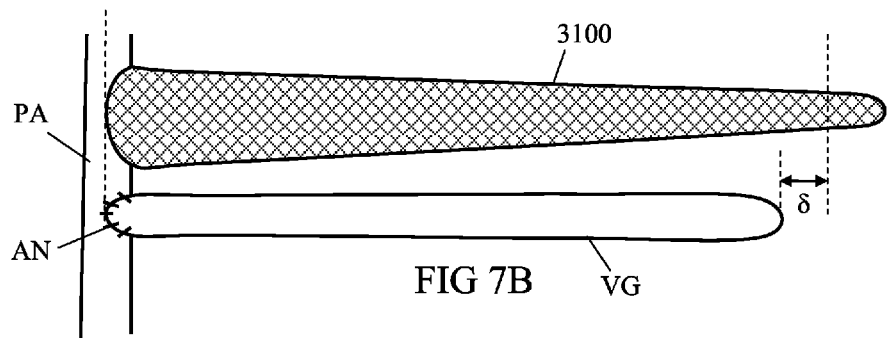

In a first step shown in FIG. 7B, after a proximal anastomosis of vein graft VG, external support 3100 is fully extended to its relaxed length, optionally manually or by external means (such as previously shown extender 200) and is then cut according to graft VG length, while optionally allowing an incremental length δ that may be predetermined. In some embodiments, in order to more accurately assess the actual length of graft VG, the latter is first at least partially inflated, for example by preserving a pressurized amount of saline therein or by inflating an elongated balloon therein (not shown). Optionally, this is done in parallel or in the framework of a routine procedure to check leaks and suture openings along the length of the graft.

Figure 7C:
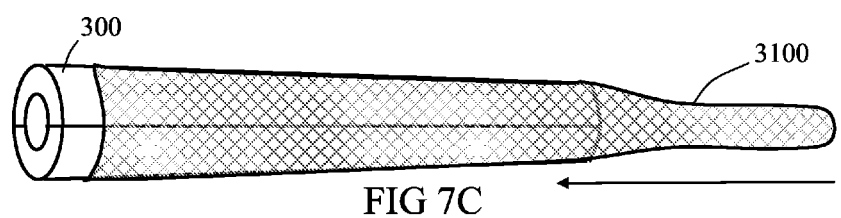
Figure 7D:
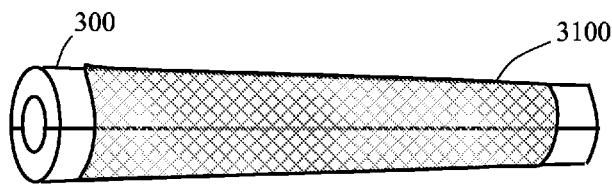

After cutting external support 3100 to a chosen length, it is then pulled over the outer boundaries of elongated body 310 causing it to stretch open to a wider diameter. While forcing its deployment on delivery device 300, the braided external support 3100 is subsequently forced to compress to a substantially shorter length, optionally less than 50% or even than 30% of its initial relaxed length. FIG. 7C shows an interim phase of deployment, whereas FIG. 7D shows a final deployment status.

Figure 7E:
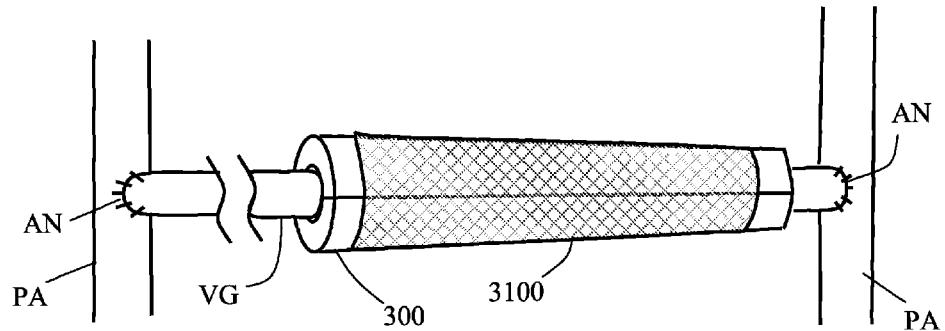
Figure 7F:
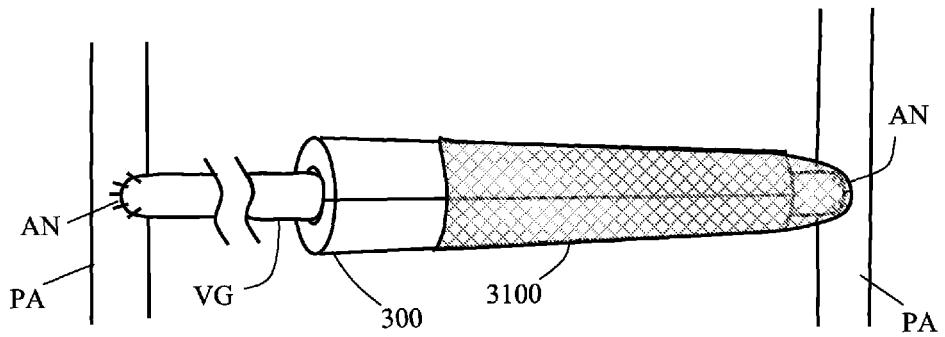
Figure 7G:
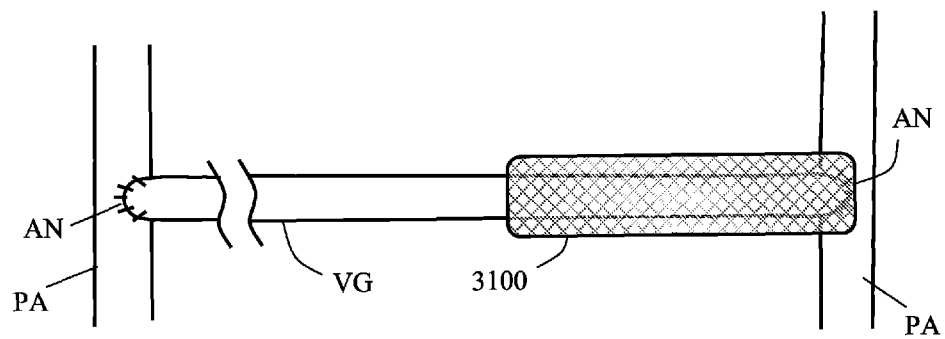

As shown in FIG. 7E, the delivery device 300 equipped with external support 3100 is then placed over vein graft VG and afterwards a distal anastomose is made. After vein graft VG is connected to the arterial system and blood flows therethrough, the surgeon may them extend external support 3100 distally while pulling it out from delivery device 3100, as illustrated in FIG. 7F, until it is fully uncovered. As shown in FIG. 7G, the external support can then be disassembled into parts 311 and 312 and removed out of patient's body, and external support 3100 may be extended proximally until completely covering vein graft VG (not shown), optionally also covering one or two anastomosis areas.

Figure 8A:
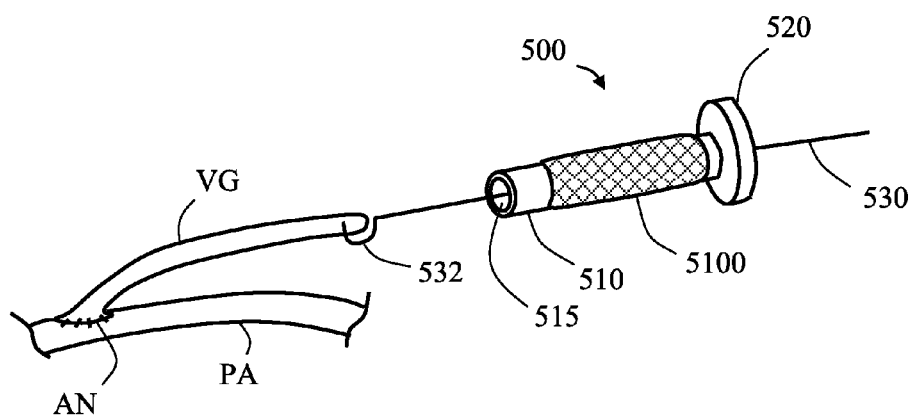
FIGS. 8A-B schematically illustrate steps in exemplary deployment of an external support over a vein graft using a manual delivery apparatus including a hook wire, in accordance with embodiments of the present invention.
Figure 8B:
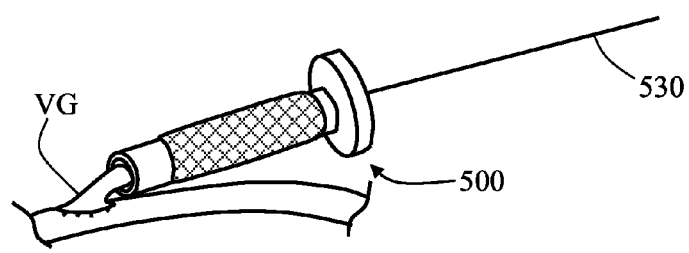

Reference is now made to FIGS. 8A-B which schematically illustrate steps in exemplary deployment of an external support 5100 over a vein graft VG using a manual delivery apparatus 500 which includes a hook wire 530, shown herein as an exemplary threading means, in accordance with embodiments of the present invention. External support 5100 may be a braided tubular mesh design, optionally any of the above described external supports. External support is shown forcefully expanded to a larger diameter onto an outer periphery 510 of delivery apparatus 500. As shown in FIG. 8A, hook wire 530 is provided through lumen 515 of delivery apparatus 500 and hooked using a hook 532 to a proximal end of vein graft VG, thereby bridging between delivery apparatus 500 and external support 5100 and allowing easy transfer of the two to and over vein graft VG. It should be noted though that other threading means capable of clinging to or grasping graft VG while extending entirely through lumen 515 may be applicable instead of hook wire 530. It should also be noted that the shown illustrations of graft VG and any other parts and instruments shown are completely out of scale and proportions and only provided as schematic illustrations. For example, in common peripheral bypass surgeries, a graft may be substantially long, and even substantially longer than length of lumen 515.

FIG. 8B shows graft VG covered (partly or fully) in lumen 515, so that the medical practitioner can now pull out and withdraw delivery apparatus 500 leaving external support 5100 covering outer periphery of graft VG. Preferably, and as previously described in previous exemplary external supports, when external supports 5100 is drawn onto graft VG it simultaneously self-extends and radially contracts to a final relaxed length (not shown).

A common practice for introducing grafts in peripheral arterial systems, for example in legs, is atraumatic or less traumatic implantation of percutaneous grafts using a tunneling system, also referred to as a tunneler. A tunneler is used to create a continuous subcutaneous passage along a chosen length of an ill artery portion and then to allow a passing through its lumen (using a dedicated hook wire or elongated grasping forceps), when extending percutaneously, the graft for final grafting and implantation. Reference is now made to FIGS. 9A-F which schematically illustrate steps in exemplary method of implanting a vein graft VG and previously shown external support 5100, using a tunneling system 600, in accordance with embodiments of the present invention.

Figure 9A:
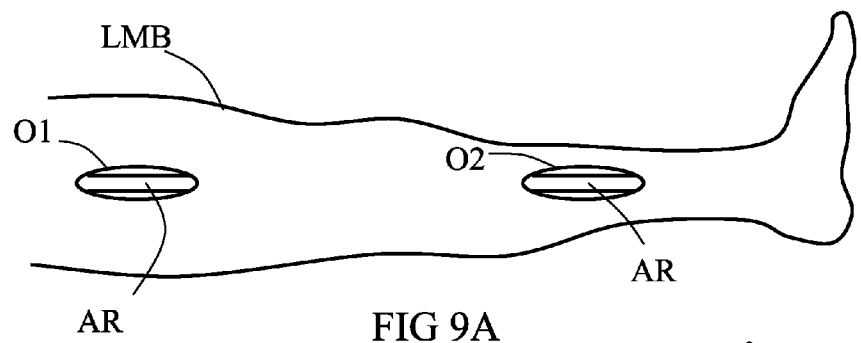
Figure 9B:
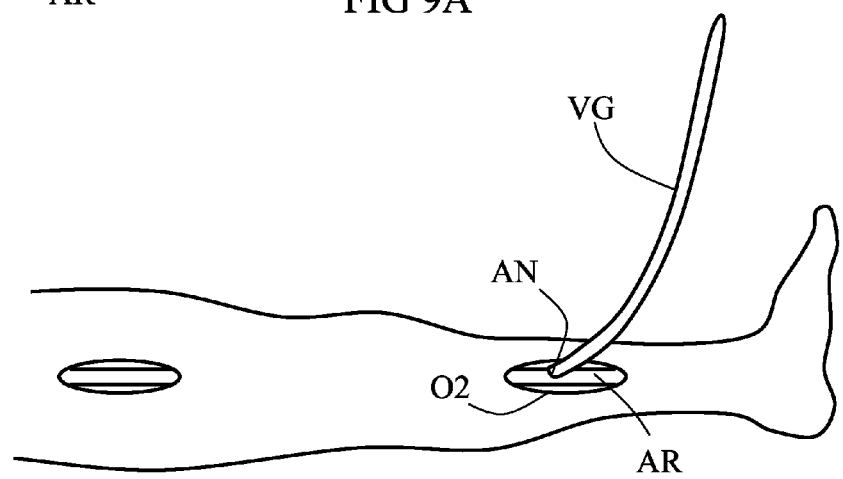
Figure 9C:
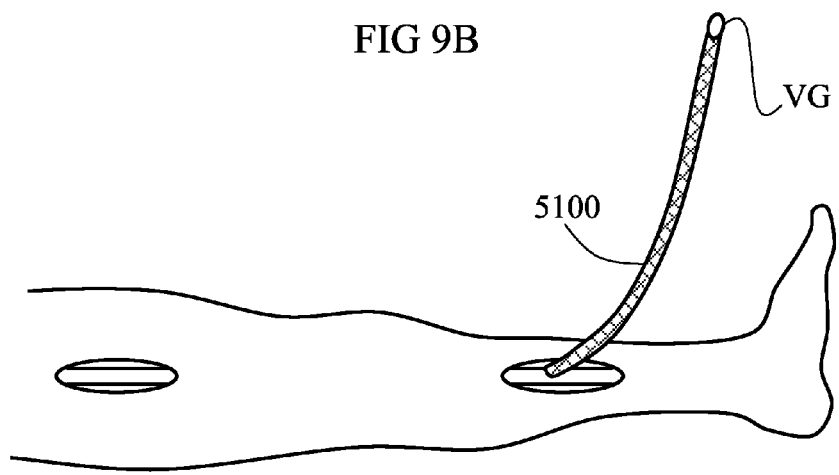

As shown in FIG. 9A, two openings—distal (O2) and proximal (O1)—are made to inferior limb LMB each exposes a different portion of an artery AR. As shown in FIG. 9B, a portion vein graft VG readily prepared for implantation (e.g., cleaned, sealed, cut to length, etc.) is first connected at one end to exposed artery AR portion, via opening O2, by anastomosis AN. External support 5100 is then introduced and deployed to cover graft VG (FIG. 9C). Covering may be made manually or by using a delivery device capable of forcing external support 5100 to take a substantially expanded diameter and/or compressed length until withdrawing and leaving external support 5100 to elastically recover back to its relaxed length and final decreased diameter along graft VG length. Delivery and/or deployment of external support 5100 may be made by any of the previously described delivery or dispensing apparatuses. Optionally, external support 5100 is manipulated to also cover anastomosis AN. Optionally, external support 5100 is manipulated to cover the entire length of graft VG; optionally to exactly cover its length or slightly over its length. Optionally and alternatively, the support is held back (optionally using grasping or other means) exposing the remaining free end of graft VG for later anastomosing. In case that external support 5100 is in excess of length, the medical practitioner may cut it to a chosen length or choose a different support. Tunneling system 600 is then introduced percutaneously (FIG. 9D) from opening O1 towards and out to opening O2 along a length of artery AR. Tunneling 600 includes a proximal end 610 and a distal end 620 and a lumen 630 traveling therebetween opened at both ends. As shown in FIG. 9E, an elongated hook wire 640 is then passed through lumen 630 from opening O1 to protrude out in opening O2 and clung or hooked to free end of the supported graft VG, pulling it into lumen 630. When pulled all the way through lumen 630 across the length of tunneling system 600, graft VG may then be anastomosed at its second end to artery AR via opening O1, as shown in FIG. 9F.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of implanting a peripheral graft, comprising:
providing an external bodily vessel support comprising:
an elongate body with a longitudinal axis and an interior to be brought into apposition with an exterior of a bodily vessel, said elongate body includes a tubular fabric of a plurality of threads, said elongate body when in a relaxed configuration has a relaxed length greater than a distance between a first end and a second end of said bodily vessel when anastomosed to a vascular system, said elongate body is sized and shaped to fit over said exterior of said bodily vessel, and said tubular fabric is longitudinally elastic to maintain said relaxed length with an axial stiffness of at least 0.1 N/m;
choosing said relaxed length so as to compress said elongate body to a compressed length when placed between said two anastomosed ends with an axial preload of at least 0.001 N;
drawing said external bodily vessel support, with said elongate body having said relaxed length and being of said size and shape to fit over said exterior of said bodily vessel, over a delivery device comprising an internal passage of at least 6 mm in diameter, including compressing said external bodily vessel support from said relaxed length to said compressed length;
threading said bodily vessel having said two ends through said passage;
externally supporting said bodily vessel by unloading said external bodily vessel support from said delivery device along said bodily vessel and into apposition therewith while regaining said relaxed configuration; and
extending said externally supported bodily vessel across a superficial percutaneous tunnel.

2. A method according to claim 1, wherein said threading is performed after anastomosing said first end.

3. A method according to claim 1, wherein said threading includes:
connecting threading means to said second end;
pulling said threading means; and
passing said delivery device over said threading means to reach said first end.

4. A method according to claim 1, wherein said superficial percutaneous tunnel is enclosed with a tunneler readily provided between surgical made openings.

5. A method according to claim 1, wherein said extending includes:
connecting threading means, provided in and along said superficial percutaneous tunnel, to said second end; and
withdrawing said threading means from said superficial percutaneous tunnel.

6. A method according to claim 1, comprising cutting said external bodily vessel support to said relaxed length being equal or greater than a final size of said bodily vessel.

7. A method according to claim 1, wherein said superficial percutaneous tunnel is made in a limb.

8. A method according to claim 1, wherein said extending is followed by anastomosing said second end.

9. A method according to claim 1, wherein said plurality of threads includes coiled compression springs.

10. A method according to claim 9, wherein said tubular fabric is longitudinally elastic to resist axial compression of said tubular fabric.

11. A method according to claim 1 wherein said tubular fabric is radially elastic to maintain a tubular shape thereof.

12. A method according to claim 1, wherein said fabric is a metal fabric.

13. A method according to claim 1, wherein said apposition is provided without curing, bonding, or external fixating means.

14. A method according to claim 1, wherein said bodily vessel is a vein graft.

15. A method according to claim 1, wherein said relaxed length is 20 cm or more.

16. A method according to claim 1, wherein said choosing said relaxed length is performed so as to compress said elongate body to said compressed length, being equal or less than said distance, when placed between said two anastomosed ends, to thereby generate said axial preload of at least 0.005 N.

17. A method according to claim 1, wherein said plurality of threads form an angle with said longitudinal axis being 50° or less at said relaxed configuration.

* * * * *